US007090838B2

(12) United States Patent
Walker et al.

(10) Patent No.: US 7,090,838 B2
(45) Date of Patent: *Aug. 15, 2006

(54) BACTERIUM NRRL B-30043 FOR CONTROLLING ALGAE

(75) Inventors: Harrell L. Walker, Ruston, LA (US); Lawrence R. Higginbotham, Ruston, LA (US)

(73) Assignee: Louisiana Tech University Foundation, Inc., Ruston, LA (US)

( * ) Notice: Subject to any disclaimer, the term of this patent is extended or adjusted under 35 U.S.C. 154(b) by 240 days.

This patent is subject to a terminal disclaimer.

(21) Appl. No.: 10/260,647

(22) Filed: Sep. 27, 2002

(65) Prior Publication Data

US 2003/0104605 A1    Jun. 5, 2003

Related U.S. Application Data

(62) Division of application No. 09/967,376, filed on Sep. 28, 2001, now Pat. No. 6,482,635, which is a division of application No. 09/228,184, filed on Jan. 11, 1999, now Pat. No. 6,322,782.

(51) Int. Cl.
| | |
|---|---|
| A01N 25/00 | (2006.01) |
| A01N 63/00 | (2006.01) |
| B09B 3/00 | (2006.01) |
| B09C 1/10 | (2006.01) |
| C12N 1/12 | (2006.01) |
| C12N 1/20 | (2006.01) |

(52) U.S. Cl. .................. 424/93.4; 424/405; 435/252.1; 435/262.5

(58) Field of Classification Search ................ 435/243, 435/252.1, 257.1, 822; 424/405, 93.1
See application file for complete search history.

(56) References Cited

U.S. PATENT DOCUMENTS

| 4,900,348 A | * | 2/1990 | Hoitink ............................. 71/6 |
| 5,348,742 A | * | 9/1994 | Howell et al. ............ 424/93.47 |
| 5,444,078 A | * | 8/1995 | Yu et al. ...................... 514/372 |
| 5,739,019 A | | 4/1998 | Walker et al. |
| 5,830,546 A | * | 11/1998 | Ehret et al. ................. 428/36.1 |

OTHER PUBLICATIONS

M. S. Armstrong, C. E. Boyd and R. T. Lovell, "Environmental factors affecting flavor of channel catfish from production ponds," *The Progressive Fish-Culturist* (1986), vol. 48, pp. 113-119.
K. H. Bowmer, A. Padovan, R. L. Oliver, W. Korth, and G. G. Ganf, "Physiology of geosmin production by *Anabaena-circinalis* isolated from the Murrumbridgee River, Australia," *Water Sci. Technol.* (1992), vol. 25(2), pp. 259-267.
C. E. Boyd, Water Quality in Warmwater Fish Ponds, *Alabama Expt. Ste./Auburn University* (1979), pp. 267-271.

C. E. Boyd, "Opportunities for management of phytoplankton in aquaculture ponds," *Proc. World Aquaculture Soc.* (1994) (Abst.) p. 69.
S. W. Brown and C. E. Boyd, "Off-flavor in channel catfish from commercial ponds," *Trans. Amer. Fish. Soc.* (1982), vol. 111, pp. 379-383.
M. J. Daft, and W. D. P. Stewart, "Bacterial Pathogens of Freshwater blue-green algae," *New Phytology.* (1971), vol. 70, pp. 819-829.
M. J. Daft, S. B. McCord and W. D. P. Stewart, "Ecological studies on algal-lysing bacteria in fresh waters," *Freshwat. Biol.* (1975), vol. 5, pp. 577-596.
N. N. Gerber, "Three highly odorous metabolites from an actinomycete: 2-isopropyl-3-methyoxypyrazine, methylisoborneaol, and geosmin," *J. Chem. Ecol.* (1977), vol. 3, pp. 475-482.
N. T. Hu, T. Thiel, T. H. Giddings, Jr., and C. P. Wolk, "New *Anabaena* and *Nostoc* cyanophages from sewage settling ponds," *Virology* (1981), vol. 114, pp. 236-246.
G. Jensen and J. Avery, "Off-flavor review and update," *The Fish Farmer* (1988), Louisiana Cooperative Extension Service, Sep., pp. 1-5.
P. B. Johnsen and J. C. W. Kuan, "Simplified method to quantify geosmin and 2-methylisoborneol concentrations in water and microbiological cultures," *J. Chromatography* (1987), vol. 409, pp. 337-342.
C. Lovejoy, J. P. Bowman and G. M. Hallegraeff, "Algicidal effects of a novel marina *Pseudoalteromonas* isolate (Class *Proteobacteria*, *Gamma* Subdivision) on harmful algal bloom species of the genera *Chattonella*, *Gymnodinium*, and *Heterosigma*," *Appl. And Envir. Microbiology* (1998), vol. 64(8), pp. 2806-2813.
R. T. Lovell and L. A. Sackey, "Absorption by channel catfish of earthy-musty flavor compounds synthesized by cultures of blue-green algae," *Trans. Amer. Fish Soc.* (1973), vol. 102, pp. 774-777.
R. T. Lovell, "Off-flavors in pond-cultured channel catfish," *Water Science and Technology* (1983), vol. 15, pp. 67-73.
J. F. Martin, G. Izaguirre, and P. Waterstrat, "A planktonic *Oscillatoria* spp. From Mississippi catfish ponds that produces the off-flavor compound 2-methylisoborneol," *Water Res.* (1991), vol. 25(12), pp. 1447-1452.

(Continued)

*Primary Examiner*—David M. Naff
*Assistant Examiner*—Deborah K. Ware
(74) *Attorney, Agent, or Firm*—Haynes and Boone, LLP

(57) ABSTRACT

A method of reducing or eliminating off-flavor in water or fish by controlling cyanobacteria or algae in the water wherein cyanobacteria or algae produce agents that cause the off-flavor. The cyanobacteria or algae are susceptible to a new Bacterium NRRL B-30043 which heretofore has not been identified or recognized as a useful agent in controlling cyanobacteria or algae. By simply treating a body of water having an off-flavor with Bacterium NRRL B-30043, the off-flavor is reduced or eliminated. Commercial fisheries or nurseries which produce channel catfish for human consumption will benefit from using this environmentally friendly Bacterium NRRL B-30043 to reduce or eliminate off-flavor in the catfish.

11 Claims, 5 Drawing Sheets

OTHER PUBLICATIONS

A. L. Mills and M. Alexander, "Microbial decomposition of species of freshwater planktonic algae," *J. Environ. Quality* (1974), vol. 3(4), pp. 423-428.

R. A. Paterson, "Parasitic and saprophytic phycomycetes which invade planktonic organisms. II. A new species of Dangeardia with notes on other *Lacustrine fungi*," *Mycologia* (1958), vol. 50(4), pp. 453-468.

E. J. Philips, R. L. Monegue and F. J. Aldridge, "Cyanophages which impact bloom-forming cyanobacteria," *J. Aquat. Plant Menage.* (1990), vol. 28, pp. 92-97.

R. S. Safferman and M. E. Morris, "Growth characteristics of the blue-green algal virus LPP-1," *Journal of Bacteriology* (1964), vol. S8(3), pp. 771-775.

R. S. Safferman and M. E. Morris, "Observations on the occurrence, distribution and seasonal incidence of blue-green algal viruses," *Applied Microbiology* (1967), vol. 15, pp. 1219-1222.

A. K. J. Sallal, N. D. Nimr and H. F. Al-Sharif, "Isolation of *Nosloc muscorum* cyanophages from a domestic sewage," *Microb. Ecol.* (1987), vol. 13, pp. 261-268.

M. Shilo, "Lysis of blue-green algae by myxobacter.," *Journal of Bacteriology* (1970), vol. 104(1), pp. 453-461.

H. C. Utkilen and M. Freshaug, "Geosmin production and excretion in a planktonic and benthic *Oscillatoria*," *Water Sci. Technol.* (1992), vol. 25(2), pp. 199-206.

M. Van der Ploeg, "Etiology of microbial off-flavors in aquaculture," *Proc. World Aquaculture Soc.* (1994), p. 71 (Abst.).

M. Van der Ploeg and C. E. Boyd, "Geosmin production by cyanobacteria blue-green algae in fish ponds at Aurburn Alabama," *J. World Aquacult. Soc.* (1991), vol. 22(4), pp. 217-226.

M. Van der Ploeg, M. E. Dennis and M. Q. de Regt., "Biology of Oscillatoria cf. Chalybea, a 2-methylisoborneol producing blue-green alga of Mississippi catfish ponds," *Water Sci. Technol.* (1995), vol. 31(11), pp. 173-180.

M. Van der Ploeg, C. S. Tucker and C. E. Boyd, Geosmin and 2-methylisoborneol production by cyanobacteria in fish ponds in the southeastern USA, *Water Sci. Technol.* (1992), vol. 25(2), pp. 283-290.

M. Van der Ploeg, C. Tucker, J. Steeby and C. Weirich, "Management plan for blue-green off-flavors in Mississippi pond-raised catfish," *Mississippi Cooperative Extension Service Publication 2001* (1996).

Walker, H. Lynn et al., "An Aquatic Bacterium That Lyses Cyanobacteria Associated with Off-Flavor of Channel Catfish (*Ictalurus punctatus*)," *Biological Control* (2000), vol. 18, pp. 71-78.

* cited by examiner

```
TGGAGAGTTTGATCCTGGCTCAGAGTGAACGCTGGCGGCAGGCCTAACACATGCAAGTCGAACGGCAGCACAGCAGTAGC
AATACTGTGGGTGGCGAGTGGCGGACGGGTGAGGAATACATCGGAATCTGCCCAGTCGTGGGGGATAACATAGGGAAACT
TATGCTAATACCGCATACGACCTACGGGTGAAAGCGGGGGATCGCAAGACCTCGCGCGATTGGATGAGCCGATGTCCGAT
TAGCTAGTTGGCGGGGTAATGGCCCACCAAGGCGACGATCGGTAGCTGGTCTGAGAGGATGATCAGCCACACTGGAACTG
AGACACGGTCCAGACTCCTACGGGAGGCAGCAGTGGGGAATATTGGACAATGGGCGCAAGCCTGATCCAGCCATGCCGCG
TGGGTGAAGAAGGCCTTCGGGTTGTAAAGCCCTTTTGTCCGGAAAGAAAAGCACTGGATTAATACTTCGGTGTTCTGACG
GTACCGGAAGAATAAGCACCGGCTAACTTCGTGCCAGCAGCCGCGGTAATACGAAGGGTGCAAGCGTTACTCGGAATTAC
TGGGCGTAAAGCGTGCGTAGGTGGTTCGTTAAGTCTGATGTGAAAGCCCTGGGCTCAACCTGGGAATTGCATTGGATACT
GGCGGGCTAGAGTGCGGTAGAGGATGGCGGAATTCCCGGTGTAGCAGTGAAATGCGTAGAGATCGGGAGGAACATCTGTG
GCGAAGGCGGCCATCTGGACCAGCACTGACACTGAGGCACGAAAGCGTGGGGAGCAAACAGGATTAGATACCCTGGTAGT
CCACGCCCTAAACGATGCGAACTGGATGTTGGGTGCAACTAGGCACTCAGTATCGAAGCTAACGCGTTAAGTTCGCCGCC
TGGGGAGTACGGTCGCAAGACTGAAACTCAAAGGAATTGACGGGGGCCCGCACAAGCGGTGGAGTATGTGGTTTAATTCG
ATGCAACGCGAAGAACCTTACCTGGCCTTGACATGCACGGAACTTTCCAGAGATGGATTGGTGCCTTCGGGAACCGTGAC
ACAGGTGCTGCATGGCTGTCGTCAGCTCGTGTCGTGAGATGTTGGGTTAAGTCCCGCAACGAGCGCAACCCTTGTCCCTA
GTTGCCAGCACGTAATGGTGGGAACTCTAGGGAGACCGCCGGCGACAAGCCGGAGGAAGGTGGGGATGACGTCAAGTCAT
CATGGCCCTTACGGCCAGGGCTACACACGTACTACAATGGTGGGGACAGAGGGCTGCAAACTCGCGAGAGTGAGCCAATC
CCAGAAACCCCATCTCAGTCCGGATTGGAGTCTGCAACTCGACTCCATGAAGTCGGAATCGCTAGTAATCGCAGATCAGC
ATTGCTGCGGTGAATACGTTCCCGGGCCTTGTACACACCGCCCGTCACACCATGGGAGTTTGTTGCACCAGAAGCAGGTA
GCTTAACCGCAAGGGGGGCGCTTGCCACGGTGTGGCCGATGACTGGGGTGAAGTCGTAACAAGGTAGCCGTATCGGAAGG
TGCGGyTGGATCACCTCCTT
```

FIG. 1

SEQUENCE LISTING

```
<160> NUMBER OF SEQ ID NOS: 1

<210> SEQ ID NO 1
<211> LENGTH: 1540
<212> TYPE: DNA
<213> ORGANISM: Unknown Organism
<220> FEATURE:
<223> OTHER INFORMATION: Bacterium SG-3;gram negative; rod-shaped;
      exhibits flagellate motility; pathogenic to cyanobacteria and
      algae; yellow colonies on BG-11 medium suppl. with trytic soy

<400> SEQUENCE: 1
tggagagttt gatcctggct cagagtgaac gctggcggca ggcctaacac atgcaagtcg      60
aacggcagca cagcagtagc aatactgtgg gtggcgagtg gcggacgggt gaggaataca     120
tcggaatctg cccagtcgtg ggggataaca tagggaaact tatgctaata ccgcatacga     180
cctacgggtg aaagcggggg atcgcaagac ctcgcgcgat tggatgagcc gatgtccgat     240
tagctagttg gcggggtaat ggcccaccaa ggcgacgatc ggtagctggt ctgagaggat     300
gatcagccac actggaactg agacacggtc cagactccta cgggaggcag cagtggggaa     360
tattggacaa tgggcgcaag cctgatccag ccatgccgcg tgggtgaaga aggccttcgg     420
gttgtaaagc ccttttgtcc ggaaagaaaa gcactggatt aatacttcgg tgttctgacg     480
gtaccggaag aataagcacc ggctaacttc gtgccagcag ccgcggtaat acgaagggtg     540
caagcgttac tcggaattac tgggcgtaaa gcgtgcgtag gtggttcgtt aagtctgatg     600
tgaaagccct gggctcaacc tgggaattgc attggatact ggcgggctag agtgcggtag     660
aggatggcgg aattcccggt gtagcagtga atgcgtaga gatcgggagg aacatctgtg     720
gcgaaggcgg ccatctggac cagcactgac actgaggcac gaaagcgtgg ggagcaaaca     780
ggattagata ccctggtagt ccacgcccta aacgatgcga actggatgtt gggtgcaact     840
aggcactcag tatcgaagct aacgcgttaa gttcgccgcc tggggagtac ggtcgcaaga     900
ctgaaactca aaggaattga cggggcccg cacaagcggt ggagtatgtg gtttaattcg     960
atgcaacgcg aagaacctta cctggccttg acatgcacgg aactttccag agatggattg    1020
gtgccttcgg gaaccgtgac acaggtgctg catggctgtc gtcagctcgt gtcgtgagat    1080
gttgggttaa gtcccgcaac gagcgcaacc cttgtcccta gttgccagca cgtaatggtg    1140
ggaactctag ggagaccgcc ggcgacaagc cggaggaagg tggggatgac gtcaagtcat    1200
catggccctt acggccaggg ctacacacgt actacaatgg tggggacaga gggctgcaaa    1260
ctcgcgagag tgagccaatc ccagaaaccc catctcagtc cggattggag tctgcaactc    1320
gactccatga agtcggaatc gctagtaatc gcagatcagc attgctgcgg tgaatacgtt    1380
cccgggcctt gtacacaccg cccgtcacac catgggagtt tgttgcacca gaagcaggta    1440
gcttaaccgc aagggggcg cttgccacgg tgtggccgat gactggggtg aagtcgtaac    1500
aaggtagccg tatcggaagg tgcggytgga tcacctcctt                          1540
```

BACTERIUM NRRL B-30043 FOR CONTROLLING ALGAE

This application is a divisional of U.S. patent application Ser. No. 09/967,376, filed Sep. 28, 2001, now U.S. Pat. No. 6,482,635 which is a divisional of U.S. patent application Ser. No. 09/228,184, filed Jan. 11, 1999, now U.S. Pat. No. 6,322,782, the entire disclosure of which is hereby incorporated herein by reference.

FIELD OF THE INVENTION

This invention relates to bioherbicides for controlling cyanobacteria, and more particularly, to a new bacterium and method of use thereof for the biological control of a variety of pest cyanobacteria that cause an off-flavor in water or aquatic life, such as fish, living in the water.

BACKGROUND OF THE INVENTION

Off-flavor has been identified as one of the most serious problems in the catfish industry. Off-flavor can render fish unpalatable, and thus delay the harvesting and marketing of commercially produced fish such as channel catfish. Losses due to off-flavor often run into the thousands of dollars for each incidence of the problem, and annual losses exceed $100 million.

Off-flavor is a complex phenomenon that is related to the absorption of compounds that are produced by cyanobacteria, algae, and actinomycetes. Geosmin (trans-1,10-dimethyl-trans-9-decalol) and 2-methylisoborneol (MIB) are produced by cyanobacteria and actinomycetes, and these two compounds have been shown to cause off-flavor in channel catfish. Although the roles of the various organisms and compounds are not completely understood, most geosmin off-flavor in commercially produced channel catfish has been attributed to species of *Anabaena*, while MIB off-flavor has been linked to a planktonic species identified as *Oscillatoria* cf. *chalybea*.

The concept of controlling off-flavor by management of cyanobacteria has been proposed (Van der Ploeg, M.; *Proc. World Aquaculture Soc.*, p. 71, 1994 (Abst.)), but no selective control measures have been developed. Conventional control practices include application of broad-spectrum algicides, such as copper sulfate or diurion [3-(3,4-dichlorophenyl)-1,1-dimethylurea]. The introduction of certain chemical agents to fresh water reservoirs or fisheries for the reduction, control or elimination of off-flavor can be undesirable. Alternative approaches not requiring the addition of chemical agents are preferred but almost nonexistant.

Viruses and microorganisms are involved in the population dynamics of cyanobacteria in nature, but there are no reports of attempts to use biological control technology to manage cyanobacteria in channel catfish ponds.

Thus, there remains a significant need for the development of alternate strategies for the reduction of off-flavor in fresh water supplies and in fish harvested from fresh water nurseries.

SUMMARY OF THE INVENTION

It has now been found that the novel bacterium of the invention is effective in controlling the susceptible species of cyanobacteria. In addition, the novel bacterium can control, reduce or eliminate the incidence of organisms responsible for off-flavor in commercially produced fish and fresh water, can manage the water quality of aquaculture and water supplies, and can be used in treating municipal or industrial waste.

Accordingly, one aspect of the present invention provides an isolated form of a pathogenic bacterium, or progeny thereof, capable of controlling the growth of at least one cyanobacterium, the pathogenic bacterium having a 16S rRNA gene sequence substantially homologous to that of SEQ. ID No 1.

The method of the invention employs a previously unknown pathogenic bacterium such as the Gram negative rod Bacterium SG-3 which exhibits flagellar motility. The Bacterium SG-3 has been deposited in the ARS Patent Culture Collection and assigned the number NRRL B-30043. RNA sequence data suggests a possible phylogenetic relation to the *Xanthomonas* spp.

Another aspect of the invention provides a method of reducing or eliminating off-flavor in water, fish, or other aquatic life forms in water. The method involves treating water with a cyanobacterial reducing or eliminating amount of a pathogenic bacterium or progeny thereof for a period of time sufficient to reduce or eliminate cyanobateria in the water thereby reducing or eliminating off-flavor in the water.

The pathogenic bacterium is preferably Bacterium SG-3. The off-flavor in the water, fish or other aquatic life form are usually caused by algae, cyanobacteria, undesired bacteria, or one or more metabolites, products or chemical agents thereof. In a preferred embodiment of the present invention, the method also involves preparing an aqueous suspension comprising Bacterium SG-3 or progeny thereof prior to treating the water with Bacterium SG-3.

The pathogenic bacterium is preferably present in preparations including a suspension, powder, solid, slug, freeze-dried powder, pellet, granule, cell lysate, homogenate, concentrate, diluted solution, or immobilized cell preparation. When granules containing the pathogenic bacterium are used as inoculum, the granules can be produced, for example, by pelletization of a suspension containing the bacterium. An exemplary pelletization procedure is described herein and in U.S. Pat. No. 5,739,019, the disclosure of which is hereby incorporated by reference in its entirety. These preparations of Bacterium SG-3 are suitable for corrective and preventitive applications.

When present in a composition, the pathogenic bacteria-containing composition can be formulated as a granule, spray dried solid, freeze dried solid, emulsifiable concentrate, wettable powder, dust aerosol, dry flowable powder or any other conventional formulation used in the application of algicides or herbicides to bodies of water. The Bacterium SG-3 is used in its native form as obtained from a culture or in a genetically engineered form. The genetically engineered form will preferably exhibit improved efficacy, enhanced pathogenicity, improved storage and formulation properties or enhanced host range.

The pathogenic bacterium may produce a lytic agent that can lyse a cyanobacterium, alga or undesired bacterium. The lytic agent could be a protein or chemical agent.

Another aspect of the invention provides a method for reducing or eliminating off-flavor in an aqueous waste or aquaculture. According to this aspect of the invention, the method involves inoculating aqueous waste or aquaculture with an inoculum comprising an off-flavor reducing or eliminating amount of Bacterium SG-3 or progeny thereof to form a mixture and incubating the mixture to increase a cellular titre of the bacterium in the mixture and to reduce or eliminate the off-flavor.

Yet another aspect of the invention provides a method of controlling an amount of cyanobacteria, algae or undesired bacteria in a water-containing environment. According to this aspect of the invention, the method involves treating cyanobacteria, algae or undesired bacteria with an effective amount of Bacterium SG-3 or progeny thereof for a period of time sufficient to control the amount of cyanobacteria, algae or undesired bacteria in the water-containing environment.

In addition to cyanobacteria and algae, susceptible viruses, fungi and bacteria can also be controlled by using Bacterium SG-3 in combination with chemicals, herbicides, other pathogenic agents or salt. This, still another aspect of the invention is a method for controlling cyanobacteria and *Plectonema* spp. in water by treating a body of water with an effective amount of Bacterium SG-3 and Cyanophage LPP-1 for a period of time sufficient to control the cyanobacteria and *Plectonema* spp. The artisan of ordinary skill will understand that the pathogenic bacterium of the invention is used to control other susceptible pest bacteria in water, fish or other aquatic life forms. Other susceptible pest bacteria include one or more of *Edwardsiella* spp., *Flexibacter* spp., *Aeromonas* spp., and *Pseudomonas* spp., in particular, *Edwardsiella ictaluri*, *Flexibacter columnaris*, *Aeromonas salmonicida*, *A. hydrophila*, and *A. sobria*.

A composition comprising a combination of a pathogenic bacterium and one or more other pathogenic organisms can provide control of a broader range of cyanobacteria and algae than is achieved using either alone. Thus, the present invention also provides an anti-algae or anti-cyanobacterial composition for the control of susceptible algae or susceptible cyanobacteria comprising a pathogenic bacterium, such as Bacterium SG-3 and a pathogenic virus, such as Cyanophage LPP-1 which is pathogenic toward *Plectonema* spp.

Another aspect of the present invention provides a method of producing the Bacterium SG-3. In a first method, the Bacterium SG-3 of the invention was isolated from a fresh water pond according to the methods of Example 1. In a second method, Bacterium SG-3 was produced by culturing in the exemplary growth medium described in Example 2. Bacterium SG-3 can also be harvested from bodies of water containing the bacterium.

BRIEF DESCRIPTION OF THE DRAWINGS

FIG. 1. SEQ. ID No. 1: gene sequence corresponding to the 16S rRNA of the Bacterium SG-3 of the invention.

DETAILED DESCRIPTION OF THE INVENTION

Figure 2:
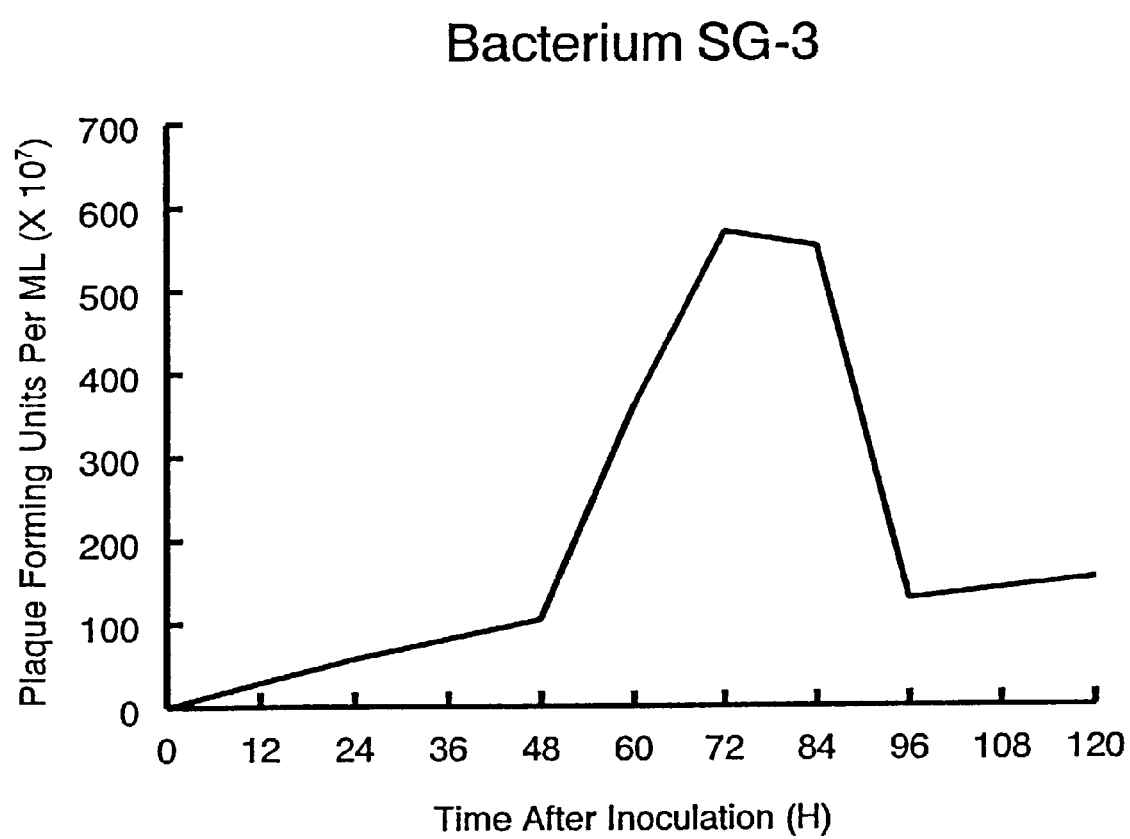
FIG. 2. Graph depicting the growth curve of Bacterium SG-3 in terms of the number of plaque forming units (PFU) of the Bacterium SG-3 produced in shake flask culture versus the time expired after inoculation.

Various aspects of the invention provide a pathogenic bacterium, a method of production thereof, and method of use thereof for controlling at least one of a cyanobacterium or alga. The term "pathogenic bacterium" refers to all of the strains and/or species which are pathogenic toward the cyanobacteria or algae in a body of water and which can be effective in reducing or eliminating off-flavor caused by the cyanobacteria or algae. A pathogenic bacterium controls at least one of the growth of, the growth rate of, and the proliferation of a susceptible cyanobacterium or algae. In reference to the pathogenicity of the pathogenic bacterium, the term "control" means to reduce, inhibit, eliminate, and/or otherwise negatively influence the cyanobacteria, algae or other susceptible organisms.

The present invention includes a number of different genera, species and strains of pathogenic bacteria which can control a susceptible cyanobacterium or alga. A preferred pathogenic bacterium is Bacterium SG-3 as described herein and related species and strains thereof as may presently or in the future be known to those of ordinary skill in the art.

The Bacterium SG-3 of the invention was isolated from cyanobacteria infected with Bacterium SG-3. However, a variety of species and strains related to Bacterium SG-3 can also be isolated from other diseased cyanobacteria or algae, that may or may not cause off-flavor in water, using the methods described herein or those commonly known to those of ordinary skill in the art. Such other cyanobacteria and algae that do not cause off-flavor in water include, by way of example and without limitation, *Microcystis*, *Raphidiopsis*, *Aphanizomenon* and *Spirulina*.

Although a particular strain and species of a pathogenic bacterium tested was isolated from cyanobacterium, the pathogenic bacterium of the invention and related species and strains isolated from other sources such as bacteria, algae, water, sediment and mud will also exhibit pathogenicity to susceptible cyanobacteria and algae. The strains of the pathogenic bacterium of the invention will generally demonstrate different degrees of pathogenicity to different cyanobacteria and algae. A host from which a particular strain of a pathogenic bacterium is isolated need not necessarily be the susceptible organism toward which the same strain demonstrates the greatest pathogenicity, e.g., a particular strain of Bacterium SG-3 may demonstrate a greater pathogenicity toward a susceptible cyanobacterium or alga other than the host from which it was isolated.

A genetically engineered pathogenic bacterium, such as a genetically engineered Bacterium SG-3, and all of its related species and strains is modified by genetic engineering using methods well known to those of ordinary skill in the art. An exemplary method of producing a genetically engineered bacterium is described in U.S. Pat. No. 5,840,554, the entire disclosure of which is hereby incorporated by reference. When used in reference to the pathogenic bacterium, the term "genetically engineered" refers to a pathogenic bacterium that has a DNA genome that has been altered from the native form of the pathogenic bacterium to include one or more foreign DNA sequences. The genetically engineered bacterium will preferably have one or more of the following properties: enhanced pathogenicity toward cyanobacteria; improved storage properties; improved formulation properties; improved growth or production characteristics; and increased spectrum of activity. A preferred genetically engineered form of the pathogenic bacterium will not express or will exhibit a reduced expression of an undesired physical property. Another preferred genetically engineered form of the pathogenic bacterium will exhibit a new property which is not native to the bacterium.

As used herein, the term "pest cyanobacteria or algae" refers to undesired or objectionable cyanobacteria or algae that grow in a body of water and cause the formation of off-flavor in the water or in fish growing in the water. Cyanobacteria and algae contemplated include, for example, *Oscillatoria* cf. *chalybea*, *Oscillatoria* spp., *Anabaena* spp., *Microcystis*, *Raphidiopsis*, *Aphanizomenon*, *Spirulina*, and others known to those of ordinary skill in the art. The term "susceptible cyanobacteria or algae" refers to pest cyanobacteria or algae which are susceptible to the pathogenic activity of the pathogenic bacterium of the invention.

As used herein, the term "control" means to kill, lyse, damage, eliminate, reduce the amount of or suppress the growth of or proliferation of cyanobacteria, algae or undesired bacteria. The Bacterium SG-3 is preferably used in an amount effective to kill, damage, eliminate or suppress, and thus control, the susceptible cyanobacteria and/or algae.

The pathogenic bacterium controls cyanobacteria and/or algae present in off-flavored water thereby stopping or reducing the rate of production of off-flavor causing chemical agents which are metabolites, products or chemical agents of the cyanobacteria and/or algae. Once the pathogenic bacterium has controlled the cyanobacteria or algae, the off-flavor causing agents are no longer produced by the cyanobacterium or the algae and any off-flavor causing agents in the water that remain after control of the cyanobacterium or algae are usually volatilized, metabolized, degraded, decomposed or otherwise removed from the water by other living organisms indigenous to the water or by environmental conditions present in the water. Consequently, the reduction in the amount of off-flavor agents in the water effects an overall reduction or elimination of off-flavor in the water.

Isolation and Identification of the Bacterium SG-3

The Bacterium SG-3 was isolated according to the method of Example 1. Cultures of the Bacterium SG-3 were submitted to ATCC for physiological characterization and identification. In addition, the gene sequence corresponding to the 16S rRNA of Bacterium SG-3 was determined by MIDI Labs and subsequently compared with databases containing the sequences from other bacteria.

The 16S rRNA gene sequence of Bacterium SG-3 is depicted in FIG. 1. Comparison of this gene sequence with MicroSeq, GenBank, and Ribosomal Database Project databases indicated no match with similar sequences of other bacteria. A phylogenetic tree indicated a possible relation to *Xanthomonas* spp.; however, the 16S rRNA gene sequence was not sufficiently similar to establish a genus level match.

Bacterium SG-3 was determined to be a Gram negative rod that produces yellow colonies when streaked on BG-11 medium supplemented with tryptic soy broth and solidified with 1% agar. Observations using a phase contrast microscope indicated motility characteristic of a flagellated bacterium. The bacterium exhibited limited to no growth in standard preparations (Difco) of nutrient broth (8 g per L), nutrient agar (23 g per L), tryptic soy broth (30 g per L) or tryptic soy agar (40 g per L). Bacterium SG-3 was determined to be oxidase positive and to have a weak catalase reaction.

Bacterium SG-3 was deposited on Jul. 28, 1998 in the ARS Patent Culture Collection (NRRL), Peoria, Ill., and assigned the number NRRL B-30043.

The subject cultures have been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Determination of the Growth Curve for Bacterium SG-3

The growth curve for the Bacterium SG-3 was determined according to the methods of Example 2 by determining the number of plaque forming units (PFU) present in serially diluted aliquots of Bacterium SG-3 shake flask cultures. Specifically, shake flask cultures (100 ml of growth medium) were inoculated with 0.1 ml from an actively growing culture of Bacterium SG-3. When assayed on *Anabaena* sp. (ATCC 27898), the number of PFU in the shake flask cultures was $8 \times 10^6$ PFU per ml, immediately following inoculation, and increased to approximately $6 \times 10^9$ PFU per ml within 72 h after inoculation (FIG. 2). The number of PFU decreased to approximately $8 \times 10^8$ PFU per ml within 96 h after inoculation. The growth curve obtained in this particular study is exemplary and not limiting of the growth curve which can be obtained with Bacterium SG-3. It will be understood by the artisan of ordinary skill that the growth curve for Bacterium SG-3 will generally vary according to the growth medium, amount of inoculum added to growth medium, pH of growth medium, shaker speed, temperature of growth medium and incubation conditions used to grow the bacterium.

Response of Selected Cyanobacteria and Algae to Bacterium SG-3

The response of selected cyanobacteria and algae to Bacterium SG-3 was determined according to the methods of Example 3. Specifically, cultures of cyanobacteria and algae were inoculated with Bacterium SG-3 and incubated for a period of time sufficient to permit the Bacterium SG-3 to control the cyanobacteria or algae. In the cyanobacteria and algae evaluated herein, the extent to which Bacterium SG-3 controls the cyanobacteria or algae was determined to be related to the extent to which it reduces the chlorophyll a content in the cyanobacteria and algae cultures. The lower the chlorophyll a content, the more effective the Bacterium SG-3 was at controlling a particular species of cyanobacteria or algae. The particular species of cyanobacteria and algae tested are summarized in Table 1.

TABLE 1

Responses of various algae and cyanobacteria to Bacterium SG-3

| Name | Source[1] | Isolate | Medium[2] | Response[3] |
|---|---|---|---|---|
| *Chlorophyceae* | | | | |
| *Chlorella vulgaris* | UTEX | 26 | BG-11 | 8 |
| *Scenedesmus subspicatus* | UTEX | 2594 | BG-11 | 0 |
| *Selenastrum capricornutum* | UTEX | 1648 | BG-11 | 1 |
| *Cyanophyceae* | | | | |
| *Anabaena* sp. | ATCC | 27892 | BG-11 | 14* |
| *Anabaena* sp. | ATCC | 27893 | BG-11 | 81** |
| *Anabaena* sp. | ATCC | 27898 | BG-11 | 98** |
| *Anabaena* sp. | ATCC | 27211 | BG-11 | 96** |
| *Anabaena aequalis* | UTEX | 1609 | BG-11 | 89** |
| *Anabaena variabilis* | UTEX | 377 | BG-11 | 97** |
| *Anabaena variabilis* | ATCC | 29413 | BG-11 | 77** |
| *Lyngbya* sp. | UTEX | 386 | BG-11 | 77** |
| *Microcystis aeruginosa* | UTEX | 2063 | BG-11 | 0 |
| *Oscillatoria* sp. | ATCC | 29205 | BG-11[4] | 98** |
| *Oscillatoria brevis* | UTEX | 1567 | BG-11[4] | 94** |
| *Oscillatoria* cf. *chalybea* | LA | OC-1 | BG-11[4] | 98** |
| *Oscillatoria lutea* var. *contorta* | UTEX | 390 | BG-11[4] | 96** |
| *Oscillatoria tenuis* | UTEX | 1566 | BG-11[4] | 97** |
| *Plectonema boryanum* | ATCC | 18200 | BG-11 | 0 |

[1]ATCC = American Type Culture Collection, Rockville, MD; UTEX = University of Texas Culture Collection, Austin, TX. LA = isolated from pond water collected from northeast Louisiana.
[2]BG-11 medium (Rippka et al. 1979)
[3]Chlorophyll a reduction (%) in shake flask cultures 7 days after inoculation with Bacterium SG-3. Comparisons were made with controls that received 1 ml of growth medium (BG-11 plus 6 g/L tryptic soy broth) only. Each value is the average of two experiments, three replications each.
[4]BG-11 medium as modified (van der Ploeg et al. 1995)
*Significant at 95% level; **Significant at 99% level according to t test. Analysis based upon respective values for µg/L chlorophyll a.

Of the algae and cyanobacteria examined 7 days after inoculation, Bacterium SG-3 reduced the chlorophyll a content primarily in species and isolates of *Anabaena* and *Oscillatoria*. A 77% reduction of chlorophyll a was noted for *Lyngbya* sp. (UTEX 386), a culture that is cross-referenced as *Oscillatoria chalybea* in the UTEX culture collection catalog. In shake flask cultures, the *Lyngbya* sp. formed aggregates and adhered to the bottom and sides of the flasks. These growth characteristics were very different from our culture of *Oscillatoria* cf. *chalybea* that exhibited growth characteristics of a planktonic species.

With the exception of one isolate, chlorophyll a reductions of the *Anabaena* spp. ranged from 77 to 98%. Reductions for *Anabaena* sp. (ATCC 27892) and *Anabaena variabilis* (ATCC 29413) were 14 and 77%, respectively, and *Anabaena variabilis* (UTEX 377) exhibited a 97% reduction.

No resistance to Bacterium SG-3 was detected in any of the *Oscillatoria* species that were tested, and chlorophyll a reductions ranged from 94 to 98%.

Although no statistically significant reductions in chlorophyll a were noted for any of the green algae, *Microcystis aeruginosa* (UTEX 2063), or *Plectonema boryanum* (ATCC 18200) inoculated solely with the particular species or strain of Bacterium SG-3 used in the exemplary evaluation, the artisan of ordinary skill will recognize that other species or strains of Bacterium SG-3 will likely be effective in controlling these particular cyanobacteria and algae.

Figure 3:
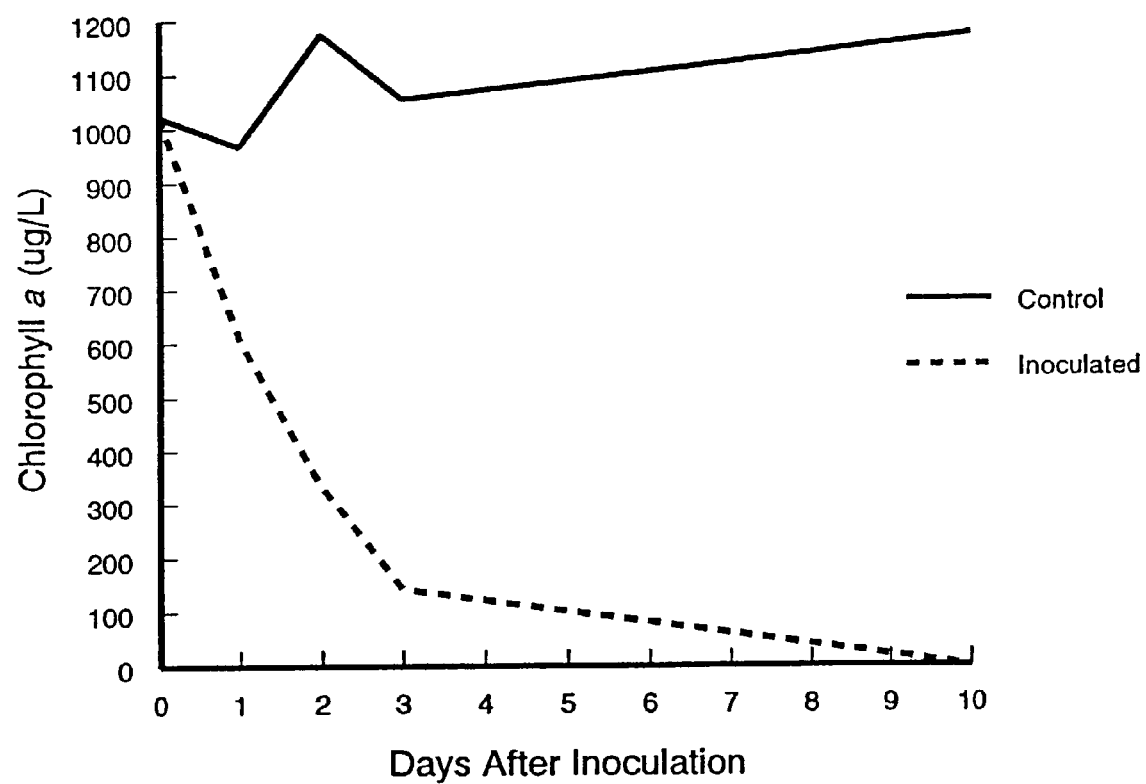
FIG. 3. Graph depicting the susceptibility of *Oscillatoria* cf. *chalybea* to the Bacterium SG-3 in terms of the effect that Bacterium SG-3 has upon chlorophyll a concentration in *Oscillatoria* cf. *chalybea* for control and treated samples.

Chlorophyll a determinations for *Oscillatoria* cf. *chalybea* at 0, 1, 2, 3, and 10 days following inoculation with Bacterium SG-3 indicated average chlorophyll a reductions of 37% and 72% within one and two days, respectively (FIG. 3). The chlorophyll a content decreased from approximately 1000 µg/L at the time of inoculation to approximately 140 µg/L within 3 days after inoculation. Clearing of inoculated cultures was evident after 24 h, and significant reductions in filament numbers in these cultures were evident from microscopic examinations.

Figure 4:
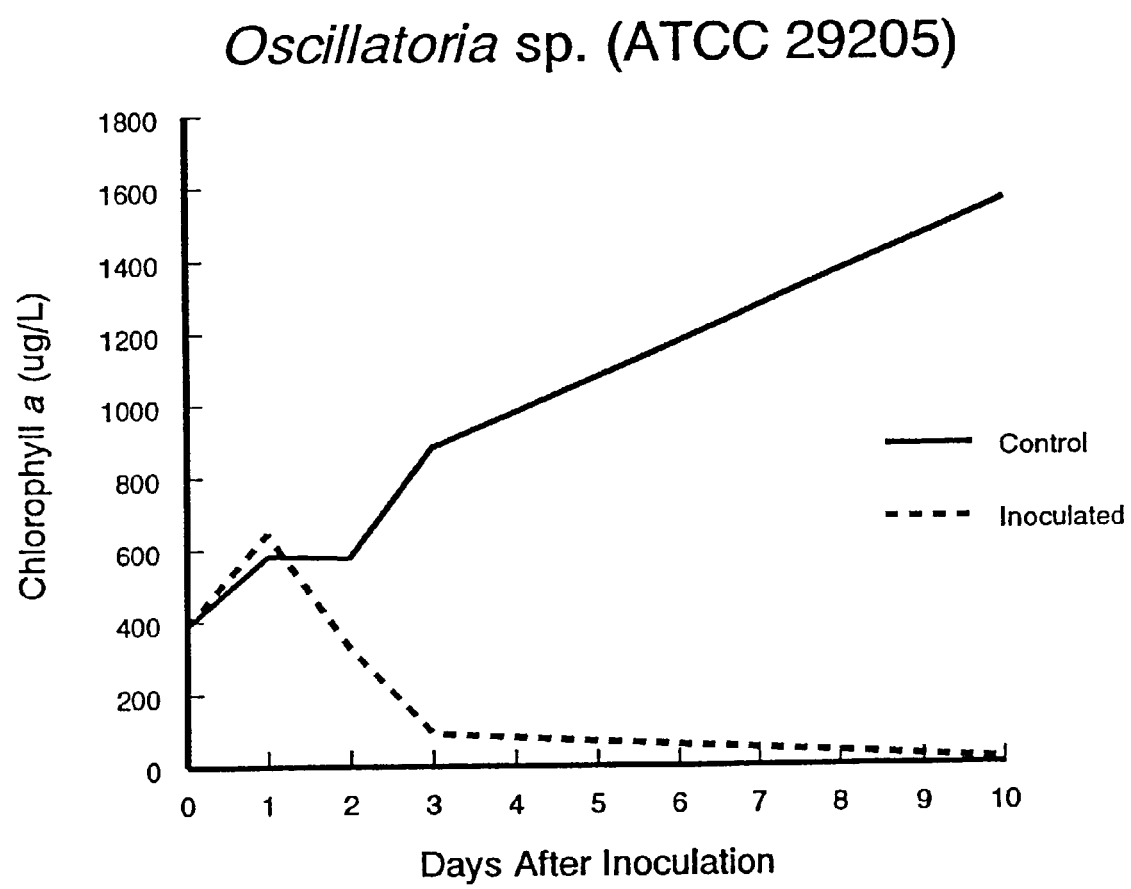
FIG. 4. Graph depicting the susceptibility of *Oscillatoria* sp. to the Bacterium SG-3 in terms of the effect that the Bacterium SG-3 has upon chlorophyll a concentration in *Oscillatoria* sp. (ATCC 29205) for control and treated samples.
Figure 5:
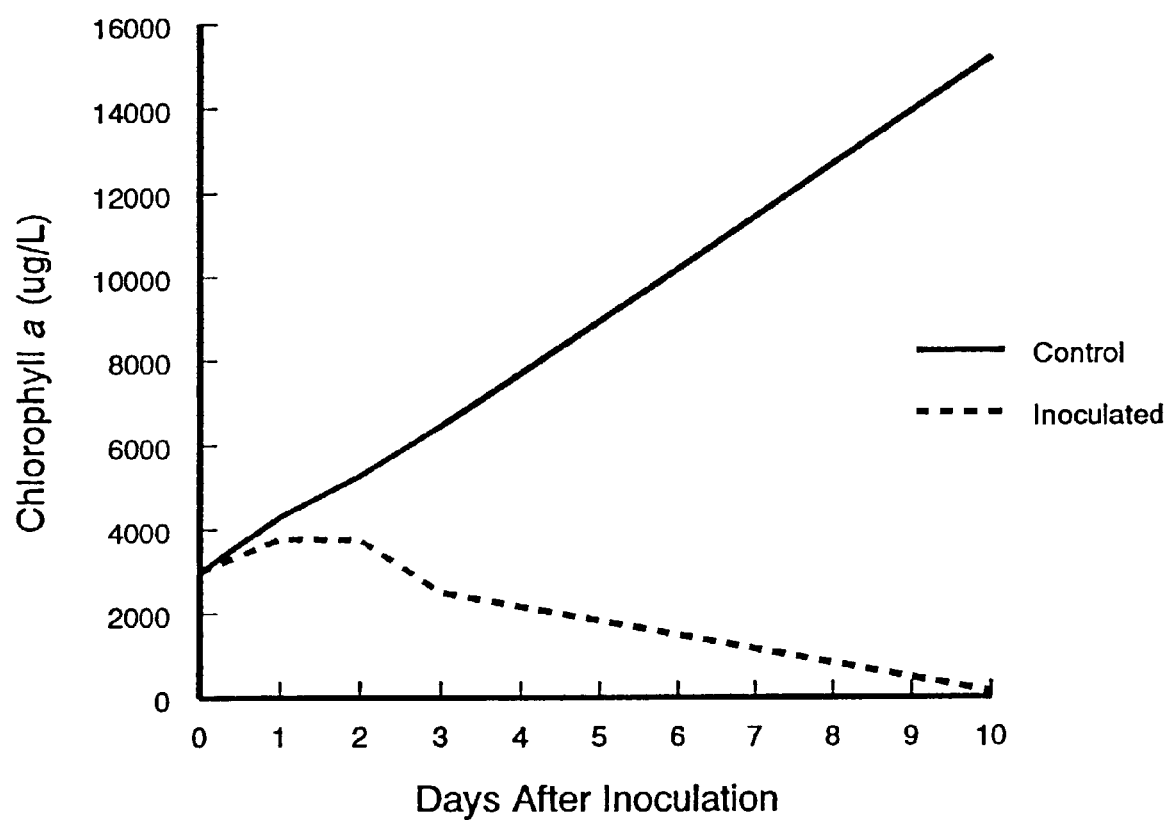
FIG. 5. Graph depicting the susceptibility of *Anabaena* sp. to the Bacterium SG-3 in terms of the effect that the Bacterium SG-3 has upon chlorophyll a concentration in *Anabaena* sp. (ATCC 27898) for control and treated samples.

Similar reductions in chlorophyll a were observed for *Oscillatoria* sp. (ATCC 29205) and *Anabaena* sp. (ATCC 27898) (FIGS. 4 and 5, respectively).

Application of Bacterium SG-3 to Pond Water

The following results were obtained when Bacterium SG-3 was applied to pond water according to Method A in Example 4 below. Initial water temperature was 29.7 C. Initial pH of the pond water in the six tanks was 8.0 to 8.2. Initial dissolved oxygen readings in the six tanks ranged from 7.5 to 8.0 ppm.

On the morning of day 2, approximately 24 hours after inoculation, the dissolved oxygen in the control tanks ranged from 3.3 to 4.5 ppm. Dissolved oxygen in the treated tanks ranged from 0.2 to 0.6 ppm. However, by the afternoon of day 3, the dissolved oxygen in the controls was >15 ppm, and the values in the treated tanks were 8.0 to 13.5 ppm.

At the conclusion of the experiment, four days after application of Bacterium SG-3, the temperature of the water was approximately 31° C. in all tanks. The pH of water in the three control tanks ranged from 9.0 to 9.4, while the pH range in the treated tanks ranged from 8.2 to 8.9. The dissolved oxygen in the three controls were >15 ppm, whereas the dissolved oxygen values for the treated tanks ranged from 9.5 to >15 ppm.

Water in the control tanks had a thick, dark green scum floating on top. The water column in the control tanks was blue-green. Dominant phytoplankton consisted of abundant *Anabaena* sp., with lesser amounts of *Microcystis* sp.

Water in the treated tanks was much clearer than the controls, and no scum was present. Microscopic examinations confirmed the absence of the *Anabaena* sp. However, *Microcystis* sp. was present.

The following results were obtained when Bacterium SG-3 was applied to pond water according to Method B in Example 4 below. Initial dissolved oxygen values for all tanks ranged from 7.8 to 8.6 ppm. Initial pH values ranged from 8.4 to 8.6. The water temperature was 28° C.

At the conclusion of experiment two, 6 days after application of Bacterium SG-3, water temperature in tanks was 31.4° C. Dissolved oxygen in all tanks ranged from 13 to >15 ppm. The pH values for the controls ranged from 9.3 to 9.9. The pH values for the 1-L and 2-L inoculated treatments were 9.4 to 9.9 and 9.2 to 9.9, respectively.

Untreated water (control tanks) remained green, and there was a thick scum on the surface. Microscopic examinations revealed the dominant phytoplankton to be *Microcystis* sp., *Oscillatoria* sp., and *Oscillatoria* cf. *chalybea*.

Water treated at the 1-L and 2-L rates of inoculum remained green, but did not exhibit the thick surface scum that was present in the untreated controls. The *Microcystis* sp. was dominant in water from both treatments and appeared to be unharmed by Bacterium SG-3.

A few isolated filaments of the *Oscillatoria* spp. were observed in water that received the 1-L treatment, but the numbers of filaments were much less than were observed in water from the control tanks. Microscopic examinations of the water that received 2-L of inoculum revealed no filaments of either species of *Oscillatoria*.

Accordingly, the present invention provides a method of reducing the amount of or eliminating cyanobacteria and/or algae in a body of water. The method involves inoculating the water with an effective amount of a pathogenic bacterium, such as Bacterium SG-3, and proliferating the pathogenic bacterium in the water for a period of time sufficient to reduce the amount of and/or eliminate the cyanobacteria or algae in the body of water. Since the cyanobacteria and algae produce chemical agents that are causative agents in the formation of off-flavor water, and thereby fish in the water, the invention provides a method of reducing and/or eliminating off-flavor in water involving substantially the same steps.

Given the demonstrated activity of the pathogenic bacterium of the invention, one of ordinary skill in the art will recognize that all of the strains of the Bacterium SG-3 can be used according to the invention for controlling susceptible cyanobacteria or algae. Thus, the present invention includes all of the strains of Bacterium SG-3. Given the biology of the pathogenic bacterium of the invention, the artisan of ordinary skill will recognize that a composition comprising whole cells, cellular fractions, lysed cells, and/or extracts, products or isolates of the pathogenic bacterium will be useful in controlling susceptible cyanobacteria or algae.

As demonstrated by the examples herein, the pathogenic bacterium of the invention is capable of selectively controlling cyanobacteria in a mixed population of cyanobacteria and algae.

Combination of Bacterium SG-3 with Other Pathogenic Agents

Bacterium SG-3 can be combined with other pathogenic agents to control a broader spectrum of cyanobacteria and algae than either agent alone. Example 5 details the evaluation of an exemplary composition for the control of mixed cultures of cyanobacteria and/or algae. The exemplary composition included a combination of Bacterium SG-3 and Cyanophage LPP-1 (ATCC 18200-B1). Mixed cultures containing Oscillatoria cf. chalybea and Plectonema boryanum (ATCC 18200) were prepared and inoculated with both Bacterium SG-3 and Cyanophage LPP-1 as described in Example 5. Then, the counts of Oscillatoria cf. chalybea and Plectonema boryanum remaining in the mixed cultures was determined. Table 2 includes the results obtained in these evaluations.

TABLE 2

Response of Mixed Cultures Containing *Oscillatoria* cf. *chalybea* and *Plectonema boryanum* (ATCC 18200) to Bacterium SG-3 and Cyanophage LPP-1 (ATCC 18200-B1)[1]

| Treatment[3] | *Oscillatoria*[2] Time after Inoculation (Days) | | | *Plectonema*[2] Time After Inoculation (Days) | | |
|---|---|---|---|---|---|---|
| | 0 | 1 | 3 | 0 | 1 | 3 |
| Controls | 769 | 868 | 1,972 | 9,367 | 10,649 | 13,804 |
| SG-3 | 769 | 0 | 0 | 9,367 | 12,719 | 12,522 |
| LPP-1 | 769 | 1,085 | 1,952 | 9,367 | 13 | 0 |
| SG-3 + LPP-1 | 769 | 0 | 0 | 9,367 | 158 | 33 |

[1]Unialgal shake flask cultures of *Oscillatoria* cf. *chalybea* and *Plectonema boryanum*, respectively, were combined (50 ml + 50 ml) in 250 ml Erlenmeyer flasks. The mixed cultures were incubated on a shaker (150 RPM) with continuous illumination from cool-white fluorescent lights.
[2]Data are filament counts determined using Sedgewick Rafter Counting Chambers. Because cells of *Oscillatoria* cf. *chalybea* are much larger than those of *Plectonema boryanum*, the number of filaments for each species could be determined. No adjustment was made to compensate for differences in lengths of filaments. Each value is the average for three replications.
[3]Cultures received either 1 ml from a three-day-old shake flask culture of Bacterium SG-3, or 1 ml of lysate produced from *Plectonema boryanum* that had been inoculated with LPP-1. Cultures inoculated with SG-3 + LPP-1 received 1 ml of Bacterium SG-3 from a Bacterium SG-3 and 1 ml of LPP-1 lysate. Controls consisted of uninoculated, mixed cultures of *Oscillatoria* and *Plectonema*.

The data clearly demonstrate that a composition comprising a combination of Bacterium SG-3 and Cyanophage LPP-1 can be used to control both *Oscillatoria* cf. *chalybea* and *Plectonema boryanum* in a mixed culture of *Oscillatoria* cf. *chalybea* and *Plectonema boryanum*. The data also demonstrate that Bacterium SG-3 can be combined with a pathogenic virus without adversely affecting the pathogenicity of either the Bacterium SG-3 or the pathogenic virus. In addition, the data demonstrate that Bacterium SG-3 can be combined with other pathogenic agents to increase or broaden the spectrum of activity over that of either the Bacterium SG-3 or the pathogenic agent alone.

The pathogenic bacterium of the invention and a chemical algicide can interact to control a pest cyanobacterium or algae or a broader range of pest cyanobacteria or algae better than either the pathogenic bacterium or algicide alone. This interaction will preferably be at least additive and more preferably be synergistic. The artisan of ordinary skill can readily devise pathogenic bacterium/algicide formulations containing the proper concentration or proportion of each in order to optimize the performance of a given formulation for a specific application. By applying both a pathogenic bacterium and algicide, the total amount required of each for controlling a pest cyanobacterium or algae will preferably be decreased.

Compositions and Formulations Containing Pathogenic Bacteria

The novel pathogenic bacterium of the invention can be utilized effectively in diverse compositions and formulations which include agronomically acceptable adjuvants and carriers normally employed for facilitating the dispersion of active ingredients in aquacultural applications. It is known that the dosage, ingredients in compositions, types of formulations, modes of application of an active agent, and other variables may affect the activity of a pathogenic agent, such as the pathogenic bacterium described herein, in any given application. Thus, the described pathogenic bacterium can be included in compositions and formulated as a suspension or dispersion in aqueous or non-aqueous media, as a dust, as a wettable powder, as an emulsifiable concentrate, as a granule, or as any of several other types of formulations known to those of ordinary skill in the art, depending on the desired mode of application. These compositions and formulations can be applied as sprays, dusts, or granules directly to the body of water to be treated.

Pellets of the pathogenic bacterium can be prepared by adding sodium alginate to a bacterial suspension from a liquid culture and dripping the resulting mixture into 0.25 M $CaCl_2$. The pathogenic bacterium can be easily recovered from the resulting pellets after air-drying the pellets. When the pellets are subsequently moistened, the bacterium will proliferate. Pellets can be suitable for storage of the pathogenic bacterium or for use as a granular formulation. Known methods for the preparation of alginate pellets including pathogenic microbes can be used to prepare alginate pellets including the pathogenic bacterium of the invention. Such known methods are disclosed, for example, in U.S. Pat. No. 4,718,935 to Walker et al, U.S. Pat. No. 4,724,147 to Marois et al, U.S. Pat. No. 4,767,441 to Walker et al and U.S. Pat. No. 4,818,530 to Marois et al the disclosures of which are hereby incorporated by reference in their entirety.

Granular application of the pathogenic bacterium is not limited to the use of alginate gel pellets, but may alternatively include granules which consist of a pathogenic bacterium and an inert carrier such as kaolin clay, corn cob grits, vermiculite and others described below. Other formulations known by those of ordinary skill in the art which are typically used in aquaculture can be used with the pathogenic bacterium herein. Such other formulations are described in a variety of texts such as *Herbicide Handbook* 5*th* *Ed*. (Weed Sciences Society of America, Champaign, Ill., 1983) the relevant disclosure of which is hereby incorporated by reference. Such formulations can include dusts, powders, flowable formulations, suspensions, emulsions, flakes, liquids, wettable powders and others known to those of skill in the art of herbicide and algicide formulations.

In order to provide compositions containing a pathogenic bacterium in the form of dusts, granules, water dispersible powders, aqueous dispersions, or emulsions and dispersions in organic liquids, the carrier or diluent agent in such formulations may be a finely divided solid, an organic liquid, water, a wetting agent, a dispersing agent, humidifying agent, or emulsifying agent, or any suitable combination of these. Generally, when liquids and wettable powders are prepared, a conditioning agent comprising one or more surface-active agents or surfactants is present in amounts sufficient to render a given composition containing the active material, the microorganism, dispersible in water or oil.

The carriers for solid formulations containing the bacterium of the invention can be either inert or active, i.e. they can either affect or not affect the pathogenicity of the pathogenic bacterium to cyanbacteria and/or algae. In an exemplary embodiment, the carrier(s) for a solid formulation also possess a desired physical property or biological activity which enhances the pathogenicity of the pathogenic bacterium to cyanobacteria and/or algae. Suitable carriers for the solid formulations of the invention include, for example, clay, talc, bentonite, calcium carbonate, diatomaceous earth, white carbon, vegetable flours, soybean flour, zeolites, kaolin clay, starch, amylopectin, cellulose, synthetic polymers, polyvinyl alcohol, polyalkylene glycol, and others known to the artisan of ordinary skill. Other substances which may be added to the formulations of the invention include, for example, sodium lignin sulfate, polyoxyethylenenonylphenyl ether, sodium dodecylbenzenesulfonate, TRITON X-100, hydrophilic (psyllium) mucilloid gel, and others known to the artisan of ordinary skill.

When referring to the solid formulation of the invention, it should be understood by the artisan of ordinary skill that physical forms such as dusts, beads, powders, particulates, pellets, tablets, agglomerates, granules, floating solids and other known solid formulations are included. The artisan of ordinary skill will be able to readily optimize a particular solid formulation for a given application using methods well known to those of ordinary skill in the art.

Since the composition of the invention can be applied as a spray utilizing a liquid carrier, it is contemplated that a wide variety of liquid carriers such as, for example, water, organic solvents, decane, dodecane, oils, vegetable oil, mineral oil, alcohol, glycol, polyethylene glycol, agents that result in a differential distribution of pathogenic bacterium in water being treated, combinations thereof and other known to artisan of ordinary skill can be used.

The present pathogenic bacterium-containing compositions can also include other substances which are not detrimental to the pathogenic bacterium such as adjuvants, surfactants, binders, stabilizers and the like, which are commonly used in agricultural and horticultural pesticides, either singly or in combination as needed.

It will be understood by the artisan of ordinary skill that various additives or agents such as, for example, nutrients, chemical herbicides and other agents that predispose the cyanobacteria or render the cyanobacteria susceptible to the pathogenic bacterium are preferably added to the inoculum preparations of pathogenic bacterium to enhance its pathogenic action. By the phrase "additive that enhances the pathogenic action of the pathogenic bacterium" is meant any compound, solvent, reagent, substance, or agent that increases the pathogenicity of the pathogenic bacterium toward cyanobacteria and/or algae as compared to the pathogenicity of the pathogenic bacterium in the absence of said additive. In some embodiments, these additives will increase the susceptibility of a particular pest cyanobacterium or alga to the pathogenic bacterium of the invention. Additional additives contemplated by the invention include, by way of example and without limitation, agents which weaken the biological defenses of susceptible pest cyanobacteria or algae to pathogens. Such agents can include salts, such as NaCl and $CaCl_2$.

Some of the pathogenic properties of the pathogenic bacterium may be attributed to toxins, products, catabolites or metabolites produced by it. Accordingly, isolation of heretofore unidentified pathogenic substances formed by the pathogenic bacterium and application of the substances to cyanobacteria or algae may prove to be an effective method in controlling the cyanobacteria or algae and off-flavor in water.

The following examples illustrate various specific aspects of the Bacterium SG-3 according to the invention.

EXAMPLE 1

Isolation of Bacterium SG-3

The Bacterium SG-3 of the invention was isolated according to previously described procedures (U.S. Pat. No. 5,739,019 to Walker et al.). Specifically, filaments of *Oscillatoria* cf. *chalybea* growing as shake flask cultures were immobilized in gel beads of calcium alginate. The immobilized *Oscillatoria* cf. *chalybea* was placed in small bags constructed from fiberglass window screen. The tops of the bags were secured with monofilament fishing line. The bags containing the beads were placed in a sampling device constructed of perforated plastic pipe (3.2×30 cm) that was capped on each end, with one cap threaded for ease of removal. After incubation at a sampling site (3 to 5 days), such as a fresh water pond, the beads of immobilized cyanobacterium were returned to the laboratory, removed from the sampling device, and placed into cultures of *Oscillatoria* cf. *chalybea*. The presence of lytic agents was indicated as zones of clearing in lawns or by destruction of filaments and cells in the shake flask cultures.

The Bacterium SG-3 obtained from the sampling device above was sub-cultured from lysate produced from inoculated shake flask cultures to form progeny of the Bacterium SG-3. Standard procedures were used to select single colonies from bacterial streaks that were made on BG-11 medium that was supplemented with tryptic soy broth (6 g/L) and solidified with 1.5% agar. After isolation, the bacterium was maintained and evaluated using this medium.

EXAMPLE 2

Determination of the Growth Curve for the Bacterium SG-3

Growth rates of the Bacterium SG-3 in shake flask cultures were quantified by determination of the number of plaque forming units (PFU). (FIG. 2) Sterile growth medium (100 ml in each of three 250 ml flasks) was aseptically inoculated with 0.1 ml from a culture of the bacterium that was 72 h old. The numbers of PFU per ml in each of three flasks were determined at 0, 24, 48, 72, 96, 120, and 144 h after inoculation. Serial dilutions of bacterial cultures were made in BG-11 medium. The growth medium was BG-11 supplemented with 6 g/L tryptic soy broth, and the host was *Anabaena* sp. (ATCC 27898). Values are averages of three replications.

Lawns of *Oscillatoria* cf. *chalybea* were difficult to prepare because of the growth characteristics of this cyanobacterium. However, the bacterium formed plaques in lawns of *Anabaena* sp. (ATCC 27898), and this isolate was used to assay for PFU.

The numbers of PFU were determined using a modification of the procedure reported by Safferman and Morris (19) for assay of cyanophages. A 5 ml overlay consisting of 0.5 ml from an appropriate dilution of the bacterial preparation, 2.0 ml from a shake flask culture of *Anabaena* sp. (ATCC 27898), and 2.5 ml of BG-11 medium (1% agar) that had been melted and cooled to approximately 47 C, was poured onto a solidified 15 ml base layer of BG-11 medium (1.5% agar). After the overlay had solidified, the cultures were inverted and incubated as previously described. Plaques developed 3–5 days after inoculation. The plaques were comprised of clear zones, typically 1 to 4 mm in diameter, with smooth margins and only minimal chlorosis at the margins. Controls consisted of overlays that included 1:100 dilutions of the growth medium. This experiment was conducted twice.

EXAMPLE 3

Evaluation of the Response of Selected Cyanobacteria and Algae to the Bacterium SG-3

Shake flask cultures (100 ml per 250 ml flask) of cyanobacteria and algae (Table 1) were inoculated with 1 ml of a Bacterium SG-3 culture that was 72 h old. Seven days after inoculation, chlorophyll a determinations were used to measure the response to Bacterium SG-3. Three shake flask cultures were inoculated for each alga or cyanobacterium. Reduction (%) of chlorophyll a was based on data from three controls that received 1 ml of growth medium only.

Chlorophyll a determinations at 0, 1, 2, 3, and 10 days following inoculation were used to evaluate the response of *Oscillatoria* cf. *chalybea*, *Oscillatoria* sp. (ATCC 29205), and *Anabaena* sp. (ATCC 27898) to the bacterium. Shake flask cultures (100 ml per 250 ml flask) were each inoculated with 1 ml from a 72 h bacterial culture. Each treatment was replicated three times, and each experiment included controls that received 1 ml of growth medium only.

EXAMPLE 4

Application of the Bacterium SG-3 to Pond Water Containing Cyanobacteria and Algae Two experiments (Methods A & B below) were conducted to study the effect of Bacterium SG-3 on naturally occurring blooms of cyanobacteria. Polypropylene tanks (800 L) were filled with 600 L of water from a commercial channel catfish pond located in northeast Louisiana. Inoculum of Bacterium SG-3 consisted of three-day-old shake flask cultures that were grown in 4 L flasks (2 L of growth medium per flask). The effects of the bacterium on bloom density and species composition were determined by visual observations and by microscopic examinations. Dissolved oxygen, conductivity and temperature readings were made with a YSI Model 85 Portable meter (YSI Incorporated, Yellow Springs, Ohio). A portable pH meter was used to make on-site measurements.

Method A. Pond water used in the first experiment contained a bloom of cyanobacteria in which the dominant species was a coiled form of *Anabaena* (tentatively identified as *A. spiroides*), with lesser numbers of a *Microcystis* sp. (tentatively identified as *M. aeruginosa*) and an *Oscillatoria* sp. (tentatively identified as *O. agardhii*). Treatments consisted of 2 L of Bacterium SG-3 inoculum per tank. Controls received 2 L of growth medium only. No aeration was used and no fish were included in this experiment. Each treatment and control was replicated three times, requiring a total of six tanks.

Method B. In the second experiment, dominant phytoplankton populations in the pond water were comprised of *Microcystis* sp., (tentatively identified as *M. aeruginosa*), a planktonic *Oscillatoria* sp. (tentatively identified as *O. agardhii*), and lesser numbers of *Oscillatoria* cf. *chalybea*. Ten channel catfish fingerlings (10 to 15 cm) were added to each tank. Bacterium SG-3 inoculum was applied at rates of 2 L and 1 L per tank. Aeration was provided (Gast ⅓ hp electric blower) and each tank was equipped with two air lines with air stones. Each treatment and control was replicated three times, which required a total of nine tanks.

EXAMPLE 5

Evaluation of a Combination Composition of Bacterium SG-3 and Cyanophage LPP-1 in Controlling a Mixed Culture of *Oscillatoria* cf. *chalybea* and *Plectonema boryanum*

Bacterium SG-3 was grown for three days as described above. Cyanophage LPP-1 was grown in a culture containing *Plectonema boryanum* as described by Safferman et al. (*J. Bacteriology* (1964), 98(3), 771–775) Unialgal shake flask cultures of *Oscillatoria* cf. *chalybea* and *Plectonema boryanum* were combined (50 ml each) in Erlenmeyer flasks. The mixed culture was incubated on a shaker (150 rpm) for a period of time with continuous illumination from cool white fluorescent lights. The mixed culture was then divided into four portions as follows: 1) control with no addition of Bacterium SG-3 or Cyanophage LPP-1; 2) inoculated with Bacterium SG-3 (1 ml from a culture flask); 3) inoculated with Cyanophage LPP-1 (1 ml of lysate from a culture flask); and 4) inoculated with Bacterium SG-3 and Cyanophage LPP-1 (1 ml of each from respective culture flasks). Following predetermined incubation periods, the

*Oscillatoria* cf. *chalybea* and *Plectonema boryanum* cell count of each portion was determined using Sedgewick Rafter Counting Chambers. Since the filaments of *Oscillatoria* cf. *chalybea* are much larger than the cells of *Plectonema boryanum*, their respective filament counts could be determined. The results are detailed in Table 2 above.

The above is a detailed description of particular embodiments of the invention. Those with skill in the art should, in light of the present disclosure, appreciate that obvious modifications of the embodiments disclosed herein can be made without departing from the spirit and scope of the invention. All of the embodiments disclosed and claimed herein can be made and executed without undue experimentation in light of the present disclosure. The full scope of the invention is set out in the claims that follow and their equivalents. Accordingly, the claims and specification should not be construed to unduly narrow the full scope of protection to which the present invention is entitled.

We claim:

1. A composition comprising at least one member selected from the group consisting of whole cells, cellular fractions, and lysed cells, of a biologically pure bacterium deposited in the ARS patent culture collection having the assigned number NRRL B-30043, wherein said composition controls at least one of a virus, a fungus, algae, and bacteria.

2. A composition according to claim 1 wherein said composition further comprises at least one member selected from the group consisting of pathogenic agents, algicides, herbicides, and additives that enhance pathogenic properties of said bacterium.

3. A composition according to claim 1 wherein said bacterium has the 16S rRNA gene sequence of SEQ.ID No. 1.

4. A composition according to claim 1 wherein said composition controls at least one of a virus, a fungus, algae, and bacteria in an aqueous environment.

5. A formulation comprising a biologically pure bacterium deposited in the ARS patent culture collection having the assigned number NRRL B-30043, wherein said formulation is selected from the group consisting of a suspension, dispersion, emulsion, powder, concentrate, granule, pellet, dust, bead, tablet, and spray.

6. A formulation according to claim 5 wherein said bacterium has the 16S rRNA gene sequence of SEQ.ID No. 1.

7. A composition comprising a biologically pure bacterium deposited in the ARS patent culture collection having the assigned number NRRL B-30043, wherein said bacterium controls at least one of a virus, fungus, and bacteria.

8. A composition according to claim 7 wherein said bacterium has the 16S rRNA gene sequence of SEQ.ID No. 1.

9. A composition according to claim 7 wherein said bacterium controls said virus, fungus, and bacteria in an aqueous environment.

10. A composition comprising at least one member selected from the group consisting of extracts and products of a biologically pure bacterium deposited in the ARS patent culture collection having the assigned number NRRL B-30043 and having the 16S rRNA gene sequence of SEQ.ID No. 1, wherein said extracts or products control at least one of algae and bacteria in an aqueous environment.

11. A composition according to claim 10 wherein said composition further comprises at least one member selected from the group consisting of pathogenic agents, algicides, herbicides, and additives that enhance pathogenic properties of said bacterium.

* * * * *